(12) United States Patent
Binder et al.

(10) Patent No.: US 12,314,446 B2
(45) Date of Patent: May 27, 2025

(54) INTEGRATED CREDENTIAL-BASED SCALABLE COMMUNICATION SYSTEM PROVIDING REMOTE ACCESS TO A PHYSICAL SITE

(71) Applicant: RRC WASHINGTON, INC., Spokane, WA (US)

(72) Inventors: Lawrence Binder, Miami, FL (US); Ryan Durgan, Spokane, WA (US); William Rhoda, Media, PA (US); Andrew Lee, Sebastopol, CA (US)

(73) Assignee: RRC WASHINGTON, INC., Spokane, WA (US)

( * ) Notice: Subject to any disclaimer, the term of this patent is extended or adjusted under 35 U.S.C. 154(b) by 39 days.

(21) Appl. No.: 18/561,255

(22) PCT Filed: May 10, 2021

(86) PCT No.: PCT/US2021/031553
§ 371 (c)(1),
(2) Date: Nov. 15, 2023

(87) PCT Pub. No.: WO2021/226577
PCT Pub. Date: Nov. 11, 2021

(65) Prior Publication Data
US 2024/0249025 A1 Jul. 25, 2024

Related U.S. Application Data

(60) Provisional application No. 63/083,604, filed on Sep. 25, 2020, provisional application No. 63/022,132, filed on May 8, 2020.

(51) Int. Cl.
G16H 40/67 (2018.01)
G06F 21/62 (2013.01)
(Continued)

(52) U.S. Cl.
CPC ......... *G06F 21/6254* (2013.01); *G16H 40/67* (2018.01); *H04N 21/21805* (2013.01); *H04N 21/23418* (2013.01); *H04N 21/25816* (2013.01)

(58) Field of Classification Search
None
See application file for complete search history.

(56) References Cited

U.S. PATENT DOCUMENTS 12,186,052 B2 * 1/2025 Brown .................. A61B 34/10
2009/0172773 A1 * 7/2009 Moore .................. G06F 16/958
705/2

(Continued)

FOREIGN PATENT DOCUMENTS

WO 2016128568 A1 8/2016

OTHER PUBLICATIONS

Supplementary European Search Report issued to European counterpart U.S. Appl. No. 21/799,611 dated Mar. 19, 2024.
(Continued)

Primary Examiner — Cai Y Chen
(74) Attorney, Agent, or Firm — McNees Wallace & Nurick LLC

(57) ABSTRACT

An integrated credential-based scalable communication system is disclosed providing remote access to a physical site. The system includes a dashboard in electronic communication with a server. The server is configured to receive an access request from a remote user, assign the remote user a credential having an access profile, and transmit an authorization request to the dashboard which displays it for approval by an authorizing agent. The server is configured to receive a live stream from the dashboard module, parse the live stream based on the access profile, and, upon approval by the authorizing agent, transmit a parsed portion of the live
(Continued)

stream to the remote user. The dashboard is configured for the authorizing agent to independently modify the access profile and credential, and terminate the live stream. The dashboard includes a switch that prevents the live stream from being transmitted by the dashboard to the server.

22 Claims, 2 Drawing Sheets

(51) Int. Cl.
    *H04N 21/218*     (2011.01)
    *H04N 21/234*     (2011.01)
    *H04N 21/258*     (2011.01)

(56) References Cited

U.S. PATENT DOCUMENTS

2013/0198005 A1    8/2013    Xiong et al.
2018/0041783 A1    2/2018    Xu

OTHER PUBLICATIONS

PCT Notification of Transmittal of the International Search Report and the Written Opinion of the International Searching Authority, or the Declaration issued to counterpart PCT Application No. PCT/US2021/031553 dated Aug. 12, 2021.

* cited by examiner

INTEGRATED CREDENTIAL-BASED SCALABLE COMMUNICATION SYSTEM PROVIDING REMOTE ACCESS TO A PHYSICAL SITE

RELATED APPLICATIONS

This application claims the benefit of and priority to U.S. Provisional Patent Application No. 63/022,132, filed May 8, 2020, entitled "Credential-Based Access to an Electronic Meeting System in a Surgical Setting," and U.S. Provisional Patent Application No. 63/083,604, filed Sep. 25, 2020, entitled "Integrated Communication and Training System, Network and Method," which are hereby incorporated by reference in their entirety.

FIELD OF THE INVENTION

The present invention is directed to the field of providing remote access to a physical site. More particularly, the present embodiments pertain to an integrated credential-based scalable communication system that provides remote access to a physical site with a live stream of audio, video, data, or combinations thereof from the physical site where access to the live stream is parsed based on access profiles keyed to credentials for remote users.

BACKGROUND OF THE INVENTION

Current technology enables participants that are physically distant from one another to have some level of presence together in an electronic forum via telephone and/or over the internet and employing one or a combination or audio-visual means. The electronic meetings are typically initiated by invitation or by directly initiated contact from one entity to one or more others.

There are inefficiencies to such modes of communication in that they do not allow for remote users to join events that are taking place in a physical location without first being invited or otherwise contacted to gain access, and they do not allow such remote users to engage with the physical location and have variable and modulated access to and control of one or more of audio, video, data, and equipment that pertain to the event in the physical location.

In addition, current technology does not include the display of third-party branding and product training capabilities that can be customized based on the participants, in particular, remote users and a physical location, in an electronic meeting system.

SUMMARY OF THE INVENTION

In accordance with various embodiments, the present invention is directed to a dashboard module, an electronic meeting participation system, for example, a surgical suite entry system, and method for providing to a remote user real time access and levels of control at a physical location, for example, within a surgical or other clinical suite wherein the access is based on preestablished credentials of the remote user as a member of a dedicated network that includes at least the remote user and the hosting physical location. The invention enables a properly credentialed remote user to gain video-based access to a physical location, such as, for example, a surgical suite. The credentialed access includes visual, auditory, data, and other in-suite information access with various levels of visual, auditory, augmented/virtual reality; or any combination thereof. The credentialed access may further include a degree of control, and provide options for the remote user to commandeer and direct the action of equipment at the physical location.

The dashboard module may provide an in-suite visual graphical interface for controlling access by remote users and optionally providing visual confirmation of the information being viewed or accessed by the remote user. The electronic meeting participation system includes the dashboard and connected computing, database, and networking capabilities, and one or more components of an audiovisual in-suite presentation screen, cameras, lighting and other controls.

In some embodiments, the electronic meeting participation system includes levels of access based on remoter user credentials that include at least one and, in some instances, more than two levels of credentialing. In some examples, the system provides for multiple levels of credentialing that include company level credentialing, hospital level credentialing, and in-suite level of credentialing. In an example, company level credentialing includes papers for Health Insurance Portability and Accountability Act of 1996 ("HIPAA") compliance, technical field, device/system specific experience, affiliation with an investigational study, and the like. Hospital level credentialing may include specific requirements of a hospital. In-suite level credentialing may include affiliation with a particular surgical team or professional or at the discretion of the in-suite director/circulator. There may be additional levels of credentialing that would include access to in-suite controls such as training requirements and the like for use of equipment, such as camera control, robotic controls, use of pointers in the room or onscreen, software control, and three-dimensional room access control.

In some embodiments, the electronic meeting participation system includes audiovisual access available to the remote user that includes a shielding functionality directed based upon one or both of an in-suite manager's control within the physical location or credential-based control. The shielding functionality actuates a blurring or distortion of a video feed or a portion of a field of view to obscure a remote user's view of all or a portion of the in-suite environment. In the instance where there are multiple video and/or audio feeds, each such feed may be differentially controlled such that the remote user's access is limited for all or only some of such feeds.

In the various embodiments, the in-suite monitoring and control of the levels of access are represented on the graphical user interface on the dashboard.

In one exemplary embodiment, an integrated credential-based scalable communication system provides remote access to a physical site. The system includes a dashboard module and a remote server control hub in electronic communication with the dashboard module and an external network. The dashboard module includes a computer having a computer processor and computer memory, an electronic display in communication with and driven by the computer, dashboard software encoded in the computer memory, and a communication port configured to receive a live stream of audio, video, data, or combinations thereof from the physical site. The remote server control hub includes a server processor, server memory, and server software encoded in the server memory. The server software is configured to receive an access request from a remote user, assign the remote user a credential having an access profile, and transmit an authorization request to the dashboard module. The dashboard software is configured to receive the authorization request and display it for approval on the electronic display for approval by an authorizing agent. The server software is configured to receive the live stream from the dashboard module, parse the live stream based on the access profile, and, upon approval by the authorizing agent, transmit a portion of the live stream corresponding to the access profile to the remote user over the external network. The dashboard software, upon commands entered by the authorizing agent, is configured to independently modify the access profile, modify the credential, and terminate the live stream. The dashboard module includes switching capabilities that prevent the live stream from being transmitted by the dashboard module to the remote server control hub. The switching capabilities may include electronic switching, physical switching, or both. Physical switching may utilize a control box that includes at least a mechanical switch that can terminate access to all content feed from the physical location. The control box may also be a hub through which all camera and other equipment feeds are controlled.

In another exemplary embodiment, a method for providing remote access to a physical site using an integrated credential-based scalable communication system incudes providing a remote server control hub and providing a dashboard module for use at a physical site. The remote server control hub is in electronic communication with an external network comprising a plurality of network participants. Each of the plurality of network participants has an access profile that corresponds with preestablished credentials for accessing live content at a physical site. The plurality of network participants include the physical site and at least one remote user. The dashboard module is operably connected with the remoter server control hub to enable the physical site to control access by the at least one remote user to the remote server control hub over the external network. The method further includes controlling the remote server control hub to activate connection with the external network to permit live communication between the physical site and the at least one remoter user over the external network. Upon receiving an access request from a remote user to access the remote server control hub at the physical site, the method includes controlling the remote server control hub to determine the remote user's credentials applicable to the physical site based on the remote user's access profile, and transmitting an authorization request to the dashboard module. Upon receiving a response to the authorization request from the dashboard module, the method further includes controlling the remote server control hub to either grant or deny access to the remote user, and, in the instance that access is granted to the remote user, controlling the remote server control hub to provide the remote user with access to receive live content controlled by the physical site based on the remoter user's credentials. The method further includes controlling the remote server control hub to simultaneously stream live content to the remote user and display live content on a communication port of the dashboard module, the live content comprising live stream of audio, video, data, or combinations thereof, the live stream originating from the physical site. Upon receiving a command from the dashboard module, the method further includes controlling the remote server control hub to suspend some or all of the live content access credentials of the remote user, or modify some or all of the live content access credentials of the remote user, or terminate the live stream to the remote user whereupon the physical site is disconnected from the external network.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
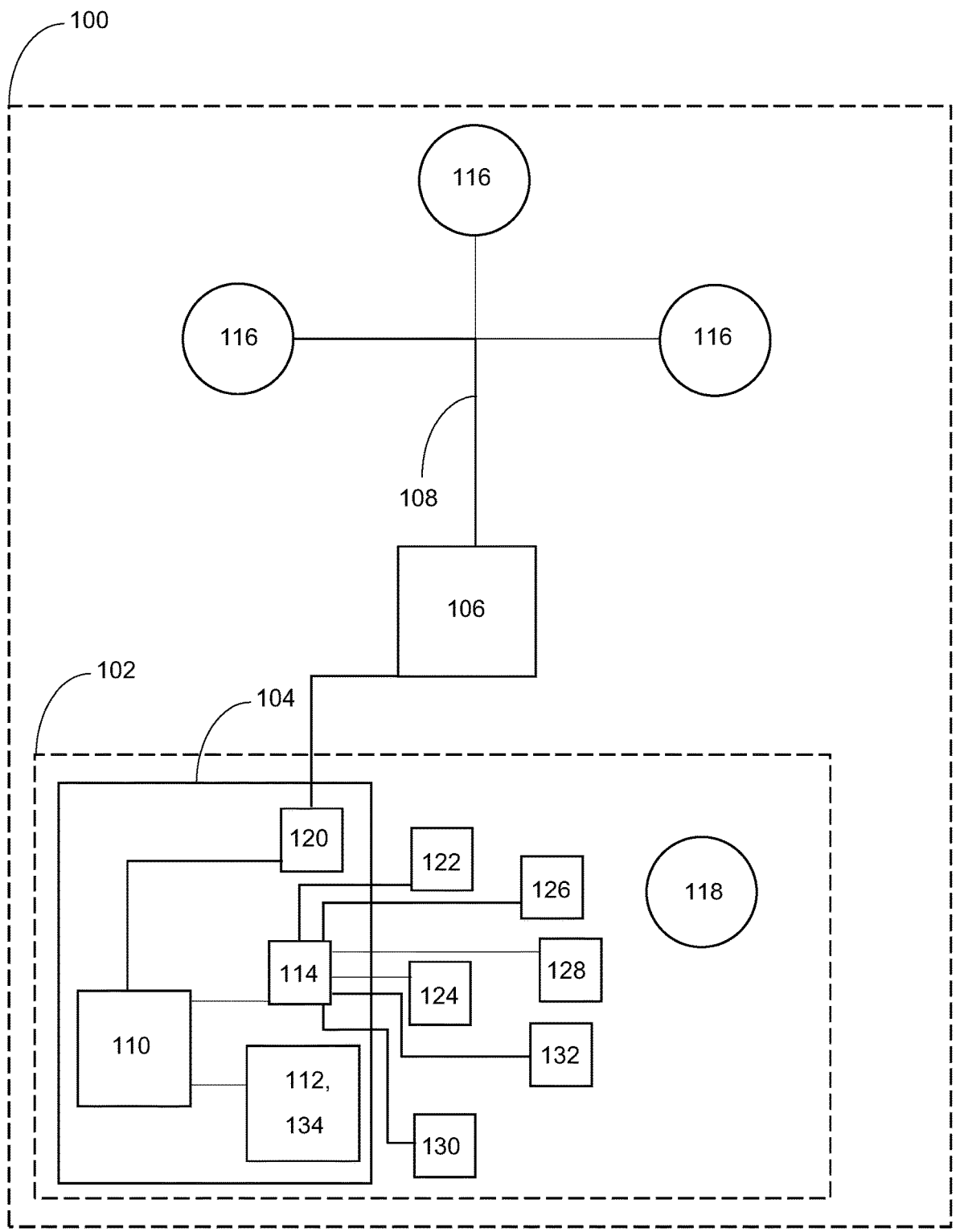
FIG. 1 illustrates an integrated credential-based scalable communication system providing remote access to a physical site, according to an embodiment of the invention. One of ordinary skill will appreciate that the illustration depicts a single remote user but contemplates that there may be any number of possible remote users.

In accordance with various embodiments, the present invention is directed to an integrated credential-based scalable communication system for providing remote access to a physical site, for example, a surgical suite entry system, and methods for providing to a remote user credentialed real time access and levels of control within a surgical or other clinical suite (also referred to as the "system"). The invention provides for a properly credentialed remote user to gain video or other-based access to a physical location, such as, for example, a surgical suite. The credentialed access may include visual, auditory, data, and other in-suite information access with various levels of control and may also provide options for a remote user to commandeer control of equipment at the physical location with on-site approval. The instant disclosure addresses elements of the system in the context of a surgical suite. It will be appreciated, however, that this is merely representative, and the invention more broadly relates to a system that enables credentialed access and levels of control to one or more remote users in the context of other physical locations and events, such as but not limited to manufacturing sites, laboratories, or other locales.

In some embodiments, the system includes levels of access based on remoter user credentials that include at least one and, in some instances, more than two levels of credentialing in an access profile. In some examples, the system provides for multiple levels of credentialing that include company level credentialing, hospital level credentialing, and in-suite level of credentialing. In one example, company level credentialing includes papers for HIPAA compliance, technical field, device/system specific experience, affiliation with an investigational study, and the like. Hospital level credentialing may include specific requirements of a hospital. In-suite level credentialing may include affiliation with a particular surgical team or professional or at the discretion of the in-suite director/circulator. There may be additional levels of credentialing that would include access to in-suite controls such as training requirements and the like for use of equipment, such as camera control, robotic controls, use of pointers in the room or onscreen, software control, and three-dimensional room access control.

In some embodiments, the electronic meeting participation system includes audiovisual access available to the remote user that includes a shielding functionality directed based upon one or both of an in-suite manager's control within the physical location or credential-based control. The shielding functionality actuates a blurring or distortion of a video feed or a portion of a field of view to obscure a remote user's view of all or a portion of the in-suite environment.

In the various embodiments, the in-suite monitoring and control of the levels of access are represented on a graphical user interface of the dashboard module.

DEFINITIONS

As used herein, certain terms will have the meanings as set forth below.

"Computer" broadly means and includes any machine comprising a processor, a memory, and an operating system, capable of interaction with a user or other computer, and includes, without limitation, desktop computers, notebook computers, laptop computers, servers, tablet computers, handheld computers, smart phones, personal digital assistants, hybrids of any of the foregoing (such as Chromebooks), and similar devices that use and/or store data.

"Local" pertains to a relationship between two or more computer/electronic devices wherein the devices are physically located in a small geographic area, for example at the physical location, such as a home, office, or a building, and communicate with each other over a local area network or without using a network, such as by wired or wireless mechanisms. Remote pertains to a relationship that is not local, such as communication over a wide area network, global network, or combinations thereof.

"Control" means use of the system by actuation of electronic devices to control any one or more audiovisual data feeds, visualization and or manipulation of textual and other imagery and data, control of entry and exit from the system, commandeering and physical manipulation of devices such as one or more cameras, laser pointers, lighting, robotic devices, and other instruments and devices that can be controlled by electronic means. The system is contemplated to enable control by one or more of preprogrammed levels of rights within the system based on credentials, manual granting/removal of rights by a user at a physical location and/or by a credentialed or granted remote user.

"Remote server control hub" means a central server (or multiple servers) with installed software used to control and route information (audio, video and data) based on predefined credentials, algorithms and active user decisions.

"Credential" means one or more computer-generated, company-created or user-created variables that are associated with a given user profile that allows the software and/or other users to determine, based on one or a combination of the variables, what access and controls a given user, or group of users, are permitted.

"In-suite" means and refers to the locus of any one or more of personnel, equipment, electronic devices, and other system elements that are at the physical location.

"Participant" means and refers to the entities and individuals participating in an electronic meeting, including at least one of each of a physical location and a remote user. In some instances, a remote user is affiliated with an entity, such as a company, and as such, the company is also a participant based on representation by the remote user and optionally the inclusion of logos, branding and other content provided by such participant company.

"Physical location" means and includes any location where any activity is taking place in which a remote user's access may be desirable. In healthcare environments, a physical location may be at a medical care facility, including but not limited to a hospital. In such environments, the term surgical suite broadly includes a room, portion of a room, a suite of multiple rooms, such as but not limited to, an operating room, a procedure room, a dental chair, a catheter lab, a clinic, or a radiology lab.

"Real time communication" is defined as the near-simultaneous exchange of information over any type of telecommunications service from the sender to the receiver in a connection with negligible or low latency.

"Remote user" means and includes any person or group of persons who are remote from the physical location. In healthcare environments, a remote user may be any one of a drug or medical device company representative, a clinician or any one or group of persons that are affiliated with an allied healthcare entity. In some embodiments, a remote user is a drug or device representative with specialized knowledge, skills and expertise with a device or drug or system used in a surgical suite.

"Augmented reality" or "mixed reality" means an interactive experience of a real-world environment where the objects that reside in the real world are enhanced by computer-generated perceptual information, sometimes across multiple sensory modalities, including visual, auditory, haptic, somatosensory and olfactory.

"Virtual reality" means a computer-generated simulation of a three-dimensional image or environment that can be interacted with in a seemingly real or physical way by a person using special electronic equipment, such as a helmet with a screen inside or gloves fitted with sensors.

Integrated Credential-Based Scalable Communication System

Figure 2:
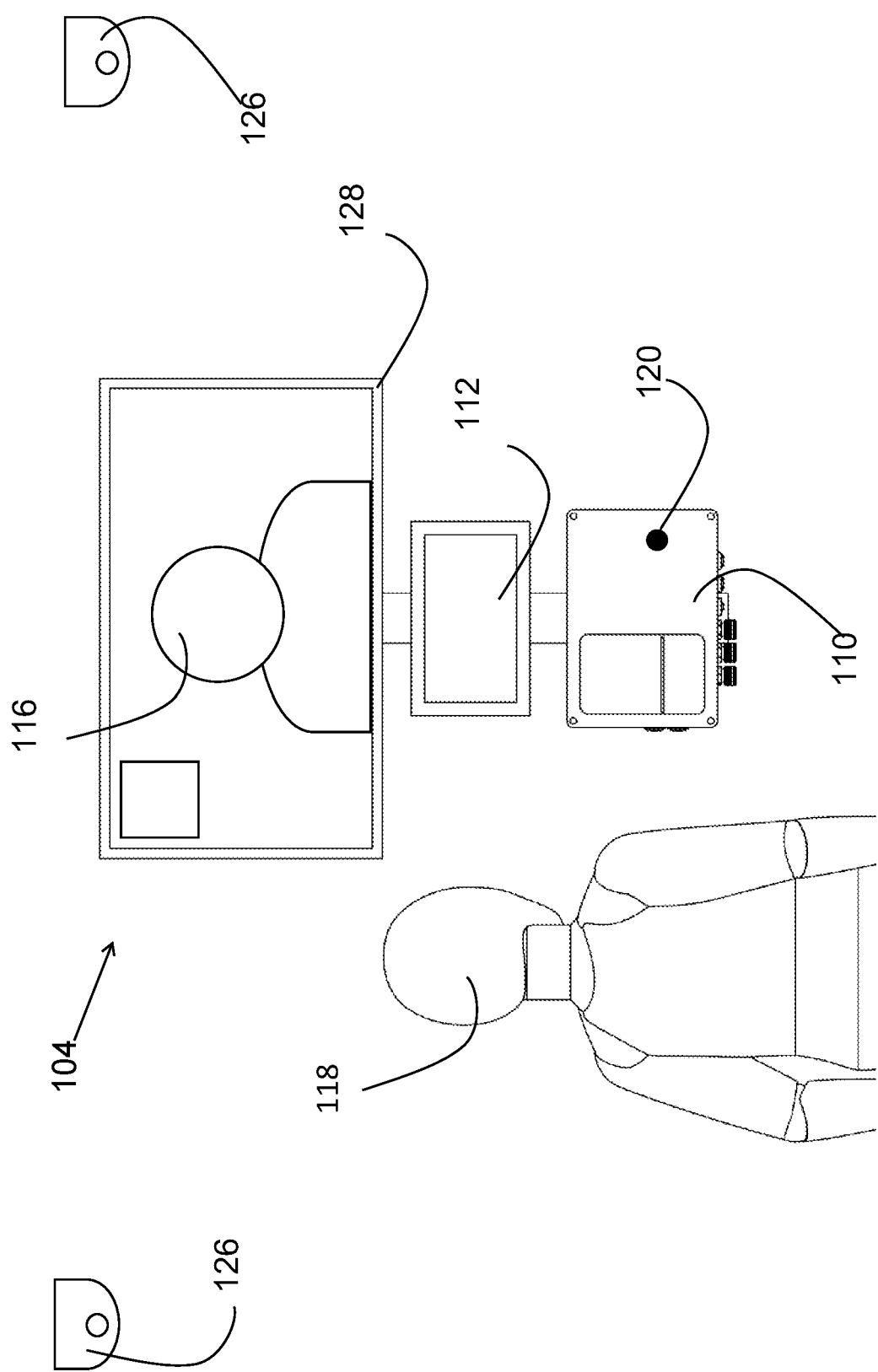
FIG. 2 illustrates an individual interacting with a remote user through an integrated credential-based scalable communication system, according to an embodiment of the invention.

Referring to FIGS. 1 and 2, in one embodiment, an integrated credential-based scalable communication system 100 provides remote access to a physical site 102. The system 100 includes a dashboard module 104 and a remote server control hub 106 in electronic communication with the dashboard module 104 and an external network 108. The dashboard module 104 includes a computer 110 having a computer processor and computer memory, an electronic display 112 in communication with and driven by the computer 110, dashboard software encoded in the computer memory, and a communication port 114 configured to receive a live stream of audio, video, data, or combinations thereof from the physical site 102. The remote server control hub includes a server processor, server memory, and server software encoded in the server memory. The server software is configured to receive an access request from a remote user 116, assign the remote user 116 a credential having an access profile, and transmit an authorization request to the dashboard module 104. The dashboard software is configured to receive the authorization request and display it for approval on the electronic display 112 for approval by an authorizing agent 118. The server software is configured to receive the live stream from the dashboard module 104, parse the live stream based on the access profile, and, upon approval by the authorizing agent 118, transmit a portion of the live stream corresponding to the access profile to the remote user 116 over the external network 108. The dashboard software, upon commands entered by the authorizing agent 118, is configured to independently modify the access profile, modify the credential, and terminate the live stream. The dashboard module 104 includes an electronic or mechanical switching function 120 that prevents the live stream from being transmitted by the dashboard module 104 to the remote server control hub 106. In some embodiments, as shown in FIG. 2, the integrated credential-based scalable communication system includes a control box 110 that includes at least a physical switch 120 operable to terminate access to all content feed from the physical location.

The live stream originates from the physical site 102. However, additional live streams may be routed through the remote server control hub 106 and may be parsed by the remote server control hub 106 based on credentials or other criteria, which originate from one or more remote users 116. Such additional live streams may be routed from a first remote user 116 to one or more other remote users 116, to the physical site 102, or combinations thereof.

The physical site 102 may be any suitable location, including, but not limited to, a medical treatment suite, a surgical suite, a doctor office, a veterinary suit, or a dental suite.

The access profile may include any suitable credential factor, including, but not limited to, HIPAA rules applied to the remote user 116, technical field of the remote user 116, medical tool specific experience of the remote user 116, affiliation of the remote user 116 with an investigational study, hospital credentialing of the remote user 116, affiliation of the remote user 116 with a particular surgical team or professional, or combinations thereof.

The server software being configured to parse the live stream may include selectively blurring or masking portions of a video live steam.

The dashboard software may be configured to transmit an audio live stream to an audio output device 122 located in the physical site 102 which is received from the remote user 116 through the remote server control hub 106 when authorized by the access profile provided by the credential.

The dashboard software may be configured to transmit instructions for remote operation of one or more local devices 124 located in the physical site from the remote user 116 through the remote server control hub 106 when authorized by the access profile provided by the credential. The one or more local devices 124 may include any suitable devices, including, but not limited to, cameras, laser pointers, lighting, robotic devices, surgical instruments, or combinations thereof.

The system may include at least one camera 126 disposed in the physical site 102, the at least one camera 126 being connected to the communication port 114 and providing a video live stream to the dashboard module 104 as at least a portion of the live stream. In one embodiment, wherein the physical site 102 is a surgical suite, the at least one camera 126 is pointed toward at least one of a surgical table, a patient, an x-ray screen, a surgical site of the patient, or an administrator. The at least one camera 126 may include a plurality of cameras 126, and each of the plurality of cameras 126 may be pointed toward a different portion of the surgical suite. The server software may be configured to parse the live stream by restricting access to a camera feed from one or more of the plurality of cameras 126 in addition to or in lieu of selectively blurring or masking portions of a video live steam from any particular camera 126. In one embodiment, the at least one camera 126 has a predetermined field of view with a first portion having a lower sensitivity and a second portion having a higher sensitivity (from a privacy or confidentiality standpoint) according to the access profile of the credential, and the server software is configured to parse the live stream by selectively blurring or masking the second portion of the field of view when the access profile of the credential authorizes access to the first portion but not the second portion.

In addition to or as the electronic display 112, the system 100 may include a monitor 128 which is ceiling-mounted, a wall-mounted, a free-standing, or a projector paired with a screen that is wall-mounted, ceiling-mounted, or free-standing.

The system may further include at least one microphone 130 disposed in the physical site 102 and connected to the communication port 114 to provide an audio live stream to the dashboard module 104 as at least a portion of the live stream.

The server software may be configured to receive a plurality of access requests from a plurality of remote users 116, assign each of the plurality of remote users 116 a user-specific credential having a user-specific access profile, and transmit a user-specific authorization request for each of the plurality of remote users 116 to the dashboard module 104. The server software services a plurality of remote users 116 is configured to receive the live stream from the dashboard module 104, parse the live stream based on each user-specific access profile, and, upon approval by the authorizing agent 118, transmit a portion of the live stream corresponding to the user-specific access profile to the each of the plurality of remote users over the external network 108.

The dashboard module 104 may include an environment scanner 132 which generates a three-dimensional virtual model of the physical site 102 and provides a spatial live stream to the dashboard module 104 as at least a portion of the live stream.

The dashboard software includes an informational module which displays a branding interface 134 on the electronic display 112. The branding interface 134, when activated, pages the remote user 116 through the remote server control hub 106 with an invitation to send an access request to the remote server control hub 106. The branding interface 134 may include a plurality of selection options, and the server software may be configured to page a specific remote user 116 correlated to one of the plurality of selection options amongst a plurality of remote users 116 based on which of the plurality of selection options the authorizing agent 118 selects.

In one embodiment, wherein the physical site 102 is a surgical suite, the branding interface 134 displays at least one selectable infographic correlated to a surgical product, and activating the at least one selectable icon correlated to the surgical product pages a product representative for the surgical product as the remote user 116. The infographic may be any suitable indicia, including, but not limited to, text, a static image, a logo, a video, an icon, or combinations thereof.

Surgical Suite Entry System

In various embodiments, the integrated credential-based scalable communication system is a surgical suite entry system comprising software programs, servers, audiovisual equipment, or combinations thereof, that is used to facilitate a remote live audio and video feed access of the operating room for medical device or drug technical representatives (remote users) during surgical procedures. The surgical suite entry system allows hospital staff to grant or remove individual feed access to a requesting technical representative from inside the operating room.

In some embodiments, the surgical suite entry system includes a tablet mounted on the wall, or a floor stand. The tablet provides a dashboard for controlling the system.

In some embodiments, the surgical suite entry system includes one or more cameras on the ceiling or wall or otherwise affixed in the surgical suit. In some such embodiments, the system includes a combination of cameras on the ceiling and walls. In some embodiments, the surgical suite entry system includes cameras that are one or more of dome, bullet, puck or web style. In some embodiments, at least one camera is pointed at the surgical table (patient). In some embodiments, at least one camera is pointed at an x-ray screen. In some embodiments, at least one camera is pointed at the surgical site (on the patient). In some embodiments, at least one camera is pointed at the circulator/OR administrator. In some embodiments the surgeon is wearing an earpiece to communicate audio information directly to the surgeon. In some embodiments the surgeon is wearing a microphone that allows communication back to the users.

In some embodiments, the surgical suite entry system includes a ceiling or wall mounted TV or monitor. In some embodiments, the surgical suite entry system includes a projector. In some embodiments, the surgical suite entry system includes external microphones or internal microphones within an electronic device. In some embodiments, the surgical suite entry system is wireless, hardwired or a combination. In various embodiments, the surgical suite entry system includes a data hotspot that is cellular, or satellite-based for data transmission.

In some embodiments, the surgical suite entry system allows multiple remote users to access the same live surgical suite audiovisual feed.

In some embodiments, the surgical suite entry system allows the technical representative to access the feed of multiple healthcare rooms around the world and specific cameras within those rooms.

In various embodiments, the surgical suite entry system allows for remote monitoring of all locations and remote users virtually present in a central software.

In some embodiments, the surgical suite entry system allows hospital staff to selectively pause, blur or otherwise distort the transmission of audio, visual or both from the feed to all the remote users from inside the surgical suite. In some such embodiments, the surgical suite entry system allows hospital staff or the remote users to actuate the controls from outside the surgical suite. In some such embodiments, the block function from that blurs the camera feed and/or the technical representative display instead of blanking it completely.

In some embodiments, at least one camera in claim is worn by a person in the room to provide a first-person perspective video feed. In some embodiments, at least one camera is mounted on a person in the form of glasses, a piece of headgear or a camera mounted on the body of any person involved in the surgical procedure i.e., surgeon, scrub-tech, anesthesia coordinator, radiology coordinator, nurse, surgical assistant representative, etc.

In some embodiments, the surgical suite entry system automatically activates based on credentialing the function to selectively pause, blur, or otherwise distort the transmission of audio, visual or both from the feed to all the remote users from inside the surgical suite.

In some embodiments, one or more cameras have the ability to pan tilt or zoom. The actuation of one or more cameras may be under control of a remote user. In some embodiments, the system includes one or more 360-degree cameras that creates one or more 360-degree live video streams of the room. In some such embodiments, at least one remote user is credentialed to view one or more room video feeds from glasses, headset, embedded contact lenses projecting the live video onto the eye or projected video into the remote user's room.

In some embodiments, the surgical suite entry system allows the technical representative the ability to change one or all of camera focus locations inside the operating room remotely. In some embodiments, the surgical suite entry system allows the technical representative the ability to remotely manipulate a laser pointer, or other targeted light source, that is physically located within the surgical suite. In some embodiments, the surgical suite entry system allows hospital staff to selectively grant that ability in the surgical suite. In some embodiments, the surgical suite entry system automatically activates remote user remote control based on credentialing.

In some embodiments, the surgical suite entry system includes a lidar camera, lidar technology or similar environment scanning technology is used in the room to scan the room in real time for creating a virtual environment to be used by one or more of the remote users. In some embodiments, the surgical suite entry system includes stitching live video feeds from two or more camera feeds to create a virtual vantage point for the remote user.

Workflows

In accordance with the disclosure, the integrated credential-based scalable communication system, for example, a surgical suite entry system, allows remote users with proper credentials and key or critical skills or knowledge are able to join a surgery or other treatment activity to provide expertise, guidance and assistance to improve or achieve the surgical treatment objectives. The benefits can be appreciated by illustrated the workflow that is enabled by the instant system and method.

In accordance with the invention, the disclosed integrated credential-based scalable communication system may be employed in an exemplary embodiment in the context of a surgical procedure at a physical location that includes a surgical suite, with at least one remote user participating. The following workflows for the surgical suite and the remote user are merely representative; the steps may be varied in sequence, certain steps may be eliminated and others repeated, and additional steps may be added.

Workflow in a Surgical Suite:

On-site staff in the physical location (circulator, administrator, surgeon, etc.):

a) Enters room and switches on surgical suite entry system
    b) Input code or login on tablet interface
    c) Select one or more remote users in queue to allow access to feeds
    d) Optionally select each remote user to display user feed on room screen to verify identity
    e) Control audio and video feeds via the tablet interface
    f) Optional—"pull shades" or "raise shades" (i.e., actuate shields to information not automatically implemented by auto credentialing) as necessary
    g) Allow device control, e.g., laser control, per user, if optioned
    h) Remove remote users from feed as needed
    i) Switch off system at end of procedure
    j) Optional—re-verify remote users for next procedure One or more of the above steps may occur in varied sequence, eliminated, or repeated as needed.

Workflow for Remote User (e.g., Surgical Device Company Representative);

a) Login to the surgical suite entry system from remote location
    b) Select physical location (surgical suite) to request access to feeds by being placed in queue
    c) Optionally—Select multiple locations to have access to feeds
    d) Unselect a location to remove remote user from that queue e) Control audio and video feeds as allowed during procedure
f) Optional Pan tilt zoom on camera if allowed
g) Optional—Control laser pointer as allowed
h) Exit feed when no longer needed
i) Optional—Stay on feed for next procedure One or more of the above steps may occur in varied sequence, eliminated, or repeated as needed.

Example of Traditional In-Room Medical Device Representative Workflow:

In the typical and/or historical setting, a medical device company representative would attend a live medical procedure in person and would assist or at least guide medical personnel in the use of medical devices employed in the medical procedure. A representative example of a workflow in this setting is provided below in the context of a spinal surgical procedure. This representative workflow may be modified according to the disclosure to accommodate a remote user as a replacement to the in person medical device company representative.

a) 15-20 minutes before the case starts—check in with the nurse circulator. Then review the sets on the back table with the 1st assist scrub. Make sure sets are not contaminated and that they are all present. This includes pulling instruments for the workflow process for the case, and confirmation of implant sizes and quantity, etc.
b) Confirmation of bone graft sizes and quantities.
c) Case starts with a time out from nurse circulator (pull shade option for circulator).
d) Confirm with scrub sizes of tap or drill, implant trials, etc. Then pull sizes of implants i.e., cage/screw diameter and length (if needed).
e) Confirm Bone graft/biologics is opened and being prepared properly so that it is ready to implant as soon as possible.
f) Surgeon asks for the desired implant size (cage or screw size depending on procedure). Implant cage/screw is then confirmed and then properly assembled on specific inserter/driver.
g) Surgeon implants cage/screw.
h) Visual confirmation of implant occurs by representative from the C-arm or microscope screen.
i) Implant usage is recorded on the usage sheet. This applies to bone graft/biologics as well.
j) Visually inspect the back table and mayo stand periodically for specific instruments if needed or requested. Walk the scrub through the set on location of said instrument/s and then audibly confirming the correct instrument is in hand.
k) Repeat steps F through J until the case is completed.
l) Once all implants have been implanted by the surgeon, audibly confirm with the nurse circulator the recorded Implants on the Usage Sheet. Provide photocopy of said usage sheet.

Variations of a workflow may consist of proprietary hospital forms, going over films, etc., before a case with a surgeon to confirm specific implant sizes; however, this is subjective to specific cases.

One or more of the above steps may occur in varied sequence, eliminated, or repeated as needed.

System Elements

In various possible embodiments, the invention provides a dashboard as part of the integrated credential-based scalable communication system. The dashboard may be embodied on electronic a display of any of a variety of electronic computing devices, including but not limited to a tablet or laptop device, or a in some embodiments a video monitor that is in communication with one or more electronic computing devices. The electronic display device may have touch screen capabilities. A dashboard on an electronic display device may include a graphical user interface (GUI) for presenting information about the event taking place in the physical location, such as a surgical suite, and may include graphically represented features that include, but are not limited to, information about the clinical subject, the institution or building location, and information about the remote user(s), among other information. Interactive virtual buttons and other actuatable images may be included in the GUI and permit actuation of features and transitioning between different levels of information of the GUI.

Credential-based access to an electronic meeting system, for example, in a surgical setting is achieved based on a database content that includes information about a remote user, which data is accessed and analyzed according to an algorithm that establishes the remote user's credentials for one or more schemes or levels of access. In the healthcare environment, for example, a scheme for levels of access may include expertise level, company level, hospital/medical entity organization level, hospital/medical location level, and in-suite/OR level. Remote user information (analyzed parameters) may include but are not limited to, education, company affiliation, hospital/medical entity affiliation, technical areas of expertise, training accreditation, and approved account status with an organization, location or clinical entity.

Levels of access that may be granted to a remote user based on the algorithm may include audio only, limited audio, visual or combination, partially screened/shielded audio, visual or combination, full audio visual access, remote control access to one or more of laser pointers, cameras, lighting, device controls, robotic and combinations of these.

In some embodiments, credentialed access may be overridden, supplemented, suspended or otherwise altered by a user in-suite or remotely having system control or higher-level credentialed access.

The system includes a program that operates to implement credentialed access. The program controlling the inventive system may be written in any of various programming languages including low-level, high-level, object-oriented, or non-object-oriented languages. Alternatively, the functions of the triaged data display program may be implemented in whole or in part by computer circuits and other hardware.

In various possible embodiments, the electronic meeting participation system may be adapted to interface with an electronic health record (EHR) system, such as, for example, the Epic health record system (Epic Systems Corporation, Verona, WI). In various possible embodiments, all system elements are HIPAA compliant and adhere to the highest security standards in the market.

The electronic meeting participation system is computer-enabled and computer-implemented. Electronic devices located at each of physical and remote sites may be on a network and in electronic or wireless communication with one or more server computers. In some embodiments, the transmissions will be encrypted.

In various embodiments, the system also includes one or a variety of electronic devices, for example at least one computer. Each computer may include internal components that may include one or more processors, one or more computer-readable random access memories (RAMs), and one or more computer-readable read-only memories (ROMs) on one or more buses, and one or more operating systems and one or more computer-readable tangible storage devices. The programs for directing the inventive system may be stored on one or more of the computer-readable tangible storage devices for execution by one or more of the processors via one or more of the RAMs. Each of the computer-readable tangible storage devices may be a magnetic disk storage device of an internal hard drive or a semiconductor storage device such as ROM, erasable programmable ROM (EPROM), flash memory, or any other computer-readable tangible storage device that can store a computer program and digital information. Each set of internal components may also include a read/write (R/W) drive or interface to read from and write to one or more portable computer-readable tangible storage devices, such as a CD-ROM, DVD, memory stick, magnetic tape, magnetic disk, optical disk, or semiconductor storage device. The program controlling the inventive system may be stored on one or more of the portable computer-readable tangible storage devices, read via R/W drive, or interface and loaded into a hard drive. Each set of internal components may also include a network adapter or interface such as a transmission control protocol/internet protocol (TCP/IP) adapter card, and content and programs for operating the inventive system may be downloaded to a local computer and/or server computer from an external computer, in some examples from the control hub, via a network (for example, the Internet, a local area network or other, wide area network) and network adapter or interface. External components may include one or more of a display monitor, a keyboard, and/or a computer mouse.

Generally, electronic devices for a meeting system may include, but are not limited to, a tablet, a smart phone or other media device, a computer, a laptop computer, a desktop computer, a modem, a router, a server, or any combination thereof. In exemplary embodiments, the dashboard is displayed on a screen of a tablet of an on-site circulator.

Integrated Branding and Training System

In an exemplary embodiment, a computer-based electronic meeting system controlling electronic access to a physical site also or alternatively includes a branding display system, a computer and a first display interface at the physical site, a server networked to the branding display system and the computer and first display interface, at least one remote user electronic access device including a second display interface and located remotely from the physical site and capable of network communication with the server, and a data repository accessible by the server. The data repository contains one or more remote user parameters specific to the at least one remote user and one or more site parameters specific to the physical site. The remote user parameters establish an initial credential profile. The system also includes an application capable of analyzing the remote user and site parameters according to an algorithm to select at least one brand or advertisement for display on at least one of the first display interface and the second display interface, where the at least one brand or advertisement is displayed on the at least one of the first display interface and the second display interface.

In another exemplary embodiment, a method includes a computer receiving a request to join an electronic meeting from a remote user. The method also includes the computer accessing a data repository containing one or more remote user parameters specific to the remote user and one or more site parameters specific to the physical site. The remote user parameters establish an initial credential profile. The method further includes the computer analyzing the remote user and site parameters according to an algorithm to select at least one brand or advertisement for display on a display interface of the remote user or at the physical site. The method yet further includes the computer directing a display of the at least one brand or advertisement on the display interface.

In accordance with various embodiments, a branding display system displays third-party branding or advertising in an electronic meeting system having credential-based access.

In accordance with various embodiments, the branding displayed by the branding display system is third-party branding that is customized, such as, for example, based on the credentials of one or more remote users having credential-based access to the electronic meeting system.

In exemplary embodiments, the branding display system facilitates the targeted display of branding during an electronic meeting within the electronic meeting system. In exemplary embodiments, the branding is third-party branding or advertising, where the third party is not a participant in the electronic meeting. In some embodiments, the branding or advertising is on one or more displays in the operating room ("OR") suite. In some embodiments, the third party is not the owner, servicer, or supplier of the monitor. The third-party branding may include advertising in the operating room suite.

The third-party branding may include advertising on one or more of the monitors being used during the electronic meeting. In some embodiments, the third-party branding is displayed on one or more monitors of remote users. The third-party branding may additionally or alternatively be displayed on one or more monitors in the operating room suite. The monitors displaying advertising in the operating room suite may or may not be visible to the remote users via the camera through their monitors. The branding in the operating room may be the same or different from the branding on the remote user's monitors. The timing and the triggers for what is shown as the branding in the operating room may be the same or different from the timing and the triggers for what is shown as the branding on the remote user's monitors.

In exemplary embodiments, the presentation or display of the branding or advertising is controlled by the electronic meeting system.

In exemplary embodiments, the branding or advertising is for a service, for a product, for an individual, or for a business or company. The branding or advertising may be in the form of or may include or be associated with text, one or more static images, a logo, a video, graphics, statistics, data points, or current or updated general information, such as, for example, the current date, the current time, the current weather or weather forecast, or recent news. In some embodiments, the branding or advertising includes audio.

In some embodiments, the branding or advertising includes participant branding. In some embodiments, a participant is provided with an option to upload or otherwise provide a logo for display in association with the participant's name and optionally the participant's contact information. In some embodiments, the logo appears associated with the participant's name on the application screen of a tablet of the circulator. In some embodiments, the logo appears on the television or display monitor if one or more criteria are met. In some embodiments, the logo is the logo of the company that the participant represents. In some embodiments, the logo is the logo of the personal business of the participant. In some embodiments, the logo appears next to the participant's name on a circulator tablet.

In some embodiments, the branding or advertising includes corporate branding. In some embodiments, the corporate branding is only displayed when one or more criteria are met. In some embodiments, the criteria include the remote user being set as a primary user, the remote user having an uploaded logo file, the remote user being associated with a particular company, and payment of a fee. When the criteria have been met, the corporate logo of the remote user appears next to the remote user's name on the circulator tablet. Another display of the corporate logo may occur when the screen has been temporarily blurred or blanked. In some embodiments, the applicable audiovisual information displays on the screen in the operating room and/or on the remote users' screens. If remote users are not sharing a camera feed, the applicable audiovisual information may be displayed instead on the screen in the operating room or from corporate branding collateral.

In exemplary embodiments, the branding display system permits a corporate sponsor to upload a standard corporate logo for all participant associated with the corporate sponsor. In such embodiments, when the user camera feed is displayed on the television monitor in the operating room, it includes identifying and/or contact information for the user similar to a production bottom thirds, a news information strip being displayed, or an athlete's statistics or other information being displayed across the bottom of the screen while the athlete is being interviewed or shown.

In some embodiments, the branding or advertising is directed to the participant at the login page. In some embodiments, the branding or advertising at the login page is targeted to the participant based on the participant's demographics and/or location.

In exemplary embodiments, pricing for the displayed audiovisual, such as video, animations, screen savers, and/or pictures, on the operating room screen is time-based and or quantity-based, and may be triggered by participants in the room, geography, procedure, date, time, words said during the electronic meeting.

In exemplary embodiments, the branding display system permits a participant to upload or download information about a product being used during the surgical procedure.

In some embodiments, a method provides credentialed real time access and levels of control within a surgical or other clinical suite to a remote user. The method also selects and directs branding or advertising to be displayed to the remote user based on the credentials of the remote user. The method enables a properly credentialed remote user to gain video-based access to a physical location, such as, for example, a surgical suite. The credentialed access includes visual, auditory, data, and other in-suite information access with various levels of control and also provides options for the remote user to commandeer and direct the action of equipment at the physical location.

In some embodiments, the branding display system and method are fully automated. In some embodiments, the branding display system and method includes some initial human intervention while the artificial intelligence is accumulating training data and is trained before becoming fully automated.

In some embodiments, the electronic meeting system includes levels of access based on remoter user credentials that include at least one and, in some instances, more than two levels of credentialing. In some examples, the system provides for multiple levels of credentialing that include company level credentialing, hospital level credentialing, and in-suite level of credentialing. In an example, company level credentialing includes papers for HIPAA compliance, technical field, device/system specific experience, affiliation with an investigational study, and the like. Hospital level credentialing may include specific requirements of a hospital. In-suite level credentialing may include affiliation with a particular surgical team or professional or at the discretion of the in-suite director/circulator. There may be additional levels of credentialing that would include access to in-suite controls such as training requirements and the like for use of equipment, such as camera control, robotic controls, use of pointers in the room or onscreen, software control, and three-dimensional room access control.

In some embodiments, the electronic meeting system includes audiovisual access available to the remote user that includes a shielding functionality directed based upon one or both of an in-suite manager's control within the physical location or credential-based control. The shielding functionality actuates a blurring or distortion of a video feed or a portion of a field of view to obscure a remote user's view of all or a portion of the in-suite environment. In some embodiments, the branding display system causes a brand or an advertisement to obscure the remote user's view.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. An integrated credential-based scalable communication system providing remote access to a physical site, the system comprising:
    a dashboard module including:
        a computer having a computer processor and computer memory;
        an electronic display in communication with and driven by the computer;
        dashboard software encoded in the computer memory; and
        a communication port configured to receive a live stream of audio, video, data, or combinations thereof, the live stream originating from the physical site;
    a remote server control hub in electronic communication with the dashboard module and an external network, the remote server control hub including:
        a server processor;
        server memory; and
        server software encoded in the server memory,
    wherein:
        the server software is configured to receive an access request from a remote user, assign the remote user a credential having an access profile, and transmit an authorization request to the dashboard module;
        the dashboard software is configured to receive the authorization request and display it for approval on the electronic display for approval by an authorizing agent;

the server software is configured to receive the live stream from the dashboard module, parse the live stream based on the access profile, and, upon approval by the authorizing agent, transmit a portion of the live stream corresponding to the access profile to the remote user over the external network;

the dashboard software, upon commands entered by the authorizing agent, is configured to independently modify the access profile, modify the credential, and terminate the live stream; and the dashboard module includes a switch that prevents the live stream from being transmitted by the dashboard module to the remote server control hub.

2. The system of claim 1, wherein the physical site is a medical treatment suite.

3. The system of claim 2, wherein the medical treatment suite is a surgical suite.

4. The system of claim 3, wherein the access profile includes at least one credential factor selected from the group consisting of HIPAA rules applied to the remote user, technical field of the remote user, medical tool specific experience of the remote user, affiliation of the remote user with an investigational study, hospital credentialing of the remote user, affiliation of the remote user with a particular surgical team or professional, or combinations thereof.

5. The system of claim 1, wherein the server software being configured to parse the live stream includes selectively blurring or masking portions of a video live steam.

6. The system of claim 1, wherein the dashboard software is configured to transmit an audio live stream to an audio output device located in the physical site which is received from the remote user through the remote server control hub when authorized by the access profile provided by the credential.

7. The system of claim 1, wherein the dashboard software is configured to transmit instructions for remote operation of a local device located in the physical site from the remote user through the remote server control hub when authorized by the access profile provided by the credential.

8. The system of claim 7, wherein the local devices is selected from the group consisting of cameras, laser pointers, lighting, robotic devices, surgical instruments, and combinations thereof.

9. The system of claim 1, further including at least one camera disposed in the physical site, the at least one camera being connected to the communication port and providing a video live stream to the dashboard module as at least a portion of the live stream.

10. The system of claim 9, wherein the physical site is a surgical suite and the at least one camera is pointed toward at least one of a surgical table, a patient, an x-ray screen, a surgical site of the patient, or an administrator.

11. The system of claim 10, wherein the at least one camera includes a plurality of cameras, each of the plurality of cameras is pointed toward a different portion of the surgical suite, and the server software being configured to parse the live stream includes restricting access to a camera feed from one or more of the plurality of cameras.

12. The system of claim 9, wherein the at least one camera has a predetermined field of view with a first portion having a lower sensitivity and a second portion having a higher sensitivity according to the access profile of the credential, and the server software being configured to parse the live stream includes selectively blurring or masking the second portion of the field of view when the access profile of the credential authorizes access to the first portion but not the second portion.

13. The system of claim 1, further including a ceiling-mounted monitor, a wall-mounted monitor, a free-standing monitor, or a projector paired with a wall-mounted, ceiling-mounted, or free-standing screen.

14. The system of claim 1, further including at least one microphone disposed in the physical site, the at least one microphone being connected to the communication port and providing an audio live stream to the dashboard module as at least a portion of the live stream.

15. The system of claim 1, wherein the server software is configured to receive a plurality of access requests from a plurality of remote users, assign each of the plurality of remote users a user-specific credential having a user-specific access profile, and transmit a user-specific authorization request for each of the plurality of remote users to the dashboard module, and the server software is configured to receive the live stream from the dashboard module, parse the live stream based on each user-specific access profile, and, upon approval by the authorizing agent, transmit a portion of the live stream corresponding to the user-specific access profile to the each of the plurality of remote users over the external network.

16. The system of claim 1, wherein the dashboard module includes an environment scanner which generates a three-dimensional virtual model of the physical site, the environmental scanner providing a spatial live stream to the dashboard module as at least a portion of the live stream.

17. The system of claim 1, wherein the dashboard software includes an informational module which displays a branding interface on the electronic display, and the branding interface, when activated, pages the remote user through the remote server control hub with an invitation to send an access request to the remote server control hub.

18. The system of claim 17, wherein the branding interface includes a plurality of selection options, and the server software is configured to page a specific remote user correlated to one of the plurality of selection options amongst a plurality of remote users based on which of the plurality of selection options the authorizing agent selects.

19. The system of claim 17, wherein the physical site is a surgical suite, the branding interface displays at least one selectable infographic correlated to a surgical product, and activating the at least one selectable icon correlated to the surgical product pages a product representative for the surgical product as the remote user.

20. The system of claim 19, wherein the infographic is selected from the group consisting of text, a static image, a logo, a video, an icon, and combinations thereof.

21. A method for providing remote access to a physical site using an integrated credential-based scalable communication system, the method comprising:

providing a remote server control hub;

providing a dashboard module for use at a physical site, wherein:

the remote server control hub is in electronic communication with an external network comprising a plurality of network participants;

each of the plurality of network participants has an access profile that corresponds with preestablished credentials for accessing live content at a physical site;

the plurality of network participants include the physical site and at least one remote user; and the dashboard module is operably connected with the remoter server control hub to enable the physical site to control access by the at least one remote user to the remote server control hub over the external network;

controlling the remote server control hub to activate connection with the external network to permit live communication between the physical site and the at least one remoter user over the external network;

upon receiving an access request from a remote user to access the remote server control hub at the physical site, controlling the remote server control hub to determine the remote user's credentials applicable to the physical site based on the remote user's access profile, and transmitting an authorization request to the dashboard module;

upon receiving a response to the authorization request from the dashboard module, controlling the remote server control hub to either grant or deny access to the remote user, and, in the instance that access is granted to the remote user, controlling the remote server control hub to provide the remote user with access to receive live content controlled by the physical site based on the remoter user's credentials;

controlling the remote server control hub to simultaneously stream live content to the remote user and display live content on a communication port of the dashboard module, the live content comprising live stream of audio, video, data, or combinations thereof, the live stream originating from the physical site; and upon receiving a command from the dashboard module, controlling the remote server control hub to suspend some or all of the live content access credentials of the remote user, or modify some or all of the live content access credentials of the remote user, or terminate the live stream to the remote user whereupon the physical site is disconnected from the external network.

22. The method of claim 21, wherein the method further includes controlling access to content at the physical site by a plurality of remote users.

* * * * *